United States Patent [19]

Shoesmith

[11] Patent Number: Plant 5,278

[45] Date of Patent: Sep. 4, 1984

[54] CHRYSANTHEMUM PLANT NAMED ORGANDY

[75] Inventor: Leonard H. Shoesmith, Woking, England

[73] Assignee: Pan American Plant Company, Parrish, Fla.

[21] Appl. No.: 405,260

[22] Filed: Aug. 4, 1982

[51] Int. Cl.[3] ..... A01H 5/00

[52] U.S. Cl. ..... Plt./80

[58] Field of Search ..... Plt./80

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Organdy and particularly characterized by its flat capitulum form and decorative capitulum form and decorative capitulum type, light lavender ray floret color, diameter across face of capitulum 40–60 mm., semi-upright branching habit, with relatively long peduncles, 1.5 to 2 meter height with no long days, and by its uniform nine (9) week photoperiodic flowering response to short days.

2 Drawing Figures

The present invention comprises a new and distinct cultivar of *Chrysanthemum morifolium,* Ramat., hereinafter referred to by the cultivar name Organdy.

Organdy is a product of a planned breeding program which had the objective of creating new chrysanthemum cultivars with decorative capitulum type, light lavender ray floret color, 8 or 9 week flowering response, and with the ability to produce commercially acceptable quality in year round cut mum programs. Such traits in combination were not present in previously available commercial cultivars.

Organdy was originated from a hybridization made in a controlled breeding program in Westfield, Woking England in 1976. The male and female parents are unknown at this time.

Organdy was discovered and selected as one flowering plant within the progeny of the stated parentage by me in November, 1977 in a controlled environment in West Chicago, Ill., and given code number Sp7-611-P. The first act of asexual reproduction of Organdy was accomplished when vegetative cuttings were taken from the initial selection on February, 1978 in a controlled environment in West Chicago, Ill. by a technician working under formulations established and supervised by me. Horticultural examination of selected units initiated September, 1978 has demonstrated that the combination of characteristics as herein disclosed for Organdy are firmly fixed and are retained through successive generations of asexual reproduction.

Organdy has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Organdy which in combination distinguish this chrysanthemum as a new and distinct cultivar:

(1) Flat capitulum form.
(2) Decorative capitulum type.
(3) Pink to lavender ray floret color.
(4) Diameter across face of capitulum 40–60 mm.
(5) Long peduncles, length 105 to 230 mm.

(6) Uniform 9 week photoperiodic flowering response to short days.
(7) Height 1.5 to 2 m with no long days.
(8) Semi-upright branching habit.

Of the many commercial cultivars known to the present inventor, the most similar in comparison to Organdy is Carillon, an unpatented but commercial cultivar. Reference is made to attached Chart A which compares certain characteristics of Organdy to those same characteristics of Carillon. In general comparison to Carillon, Organdy has longer peduncles, flowers one week earlier, is taller in plant height, and has a larger diameter across the face of the capitulum than Carillon. The ray floret color, capitulum form and capitulum type are similar to those same characteristics of Carillon.

The accompanying photographic drawings show typical inflorescence and foliage characteristics of Organdy, with colors being as nearly true as possible with illustrations of this type. Sheet 1 is color photograph of Organdy in perspective. Sheet 2 is black and white photo showing the reverse side of typical foliage of Organdy at various locations and stages of growth on the plant.

In the following description color references are made to The Royal Horticultural Society Colour Chart. The color values were determined between 3:30–4:00 P.M. on May 24, 1982 under incandescent 3200K–500W light intensity at Bradenton, Fla.

CLASSIFICATION

Botanical: *Chrysanthemum morifolium,* Ramat., cv Organdy.

Commercial: Cut decorative spray or pompon.

INFLORESCENCE

Capitulum:

*Form.*—Flat.

*Type.*—Decorative.

*Diameter across face.*—40–60 mm.

Corolla of ray florets:

*Color (general tonality from a distance of* 1.5 *meters)*-.—Light lavender.

*Color (abaxial).*—69A–69D.

*Color (adaxial).*—68A–68D.

Reproductive organs:

*Androecium.*—Present disc florets only; few to none.

*Gynoecium.*—Present ray florets only; numerous.

PLANT

General appearance:

*Height.*—1.5–2 Meters given no long days year round.

Foliage:

*Color (underside).*—137D.

*Color (topside).*—137A.

*Shape.*—Deeply lobed and slightly serrated.

CHART A

COMPARISON OF ORGANDY AND CARILLON

| CULTIVAR | RAY FLORET COLOR | CAPITULUM FORM AND TYPE | NO LONG DAYS PLANT HEIGHT |
|---|---|---|---|
| ORGANDY | Dark pink to light lavender | Flat decorative about 25 mm. deep | 1.5–2 m |
| CARILLON | Dark pink to light lavender | Flat decorative about 20 mm. deep | .5–1.5 m |

CHART A-continued

COMPARISON OF ORGANDY AND CARILLON

| CULTIVAR | DIAMETER ACROSS FACE OF CAPITULUM | FLOWERING RESPONSE PERIOD | PEDUNCLE LENGTH |
|---|---|---|---|
| ORGANDY | 40–60 mm. | 9 weeks year round | 105–230 mm. |
| CARILLON | 15–45 mm. | 10 weeks year round | 100–132 mm. |

I claim:

1. A new and distinct cultivar of chrysanthemum plant known by the cultivar name Organdy, as shown and described, and particularly characterized by its flat capitulum form and decorative capitulum form and decorative capitulum type, light lavender ray floret color, diameter across face of capitulum 40–60 mm., semi-upright branching habit, with relatively long peduncles, 1.5 to 2 meter height with no long days, and by its uniform nine (9) week photoperiodic flowering response to short days.

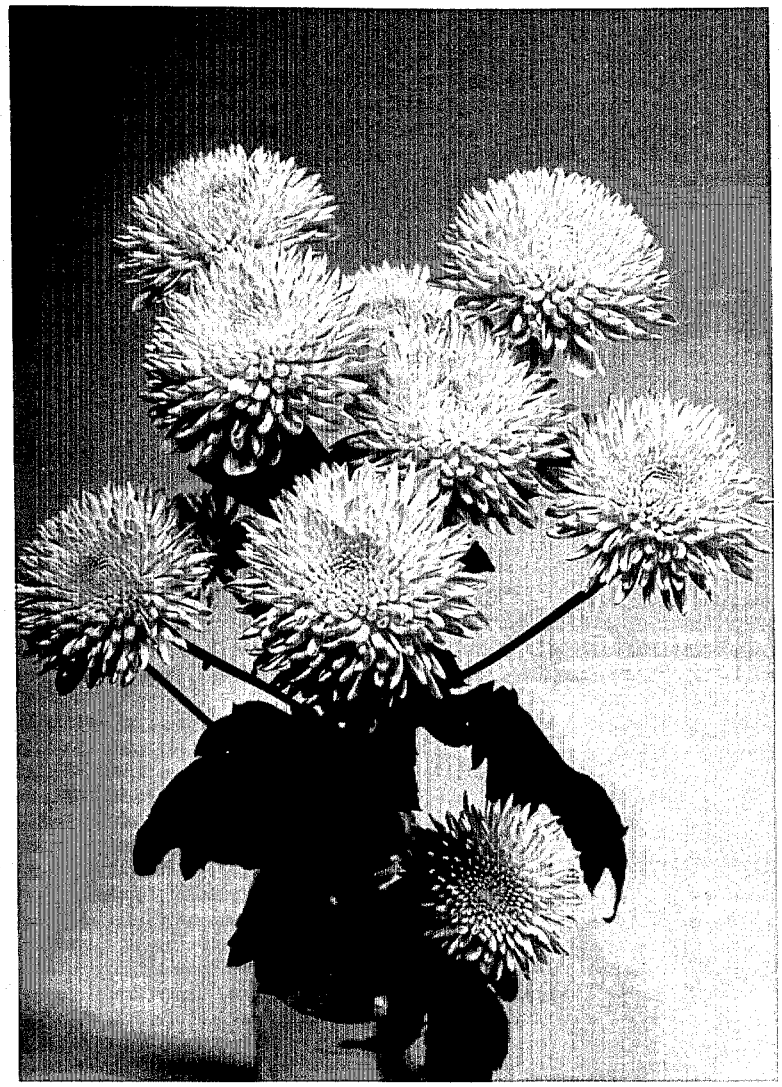

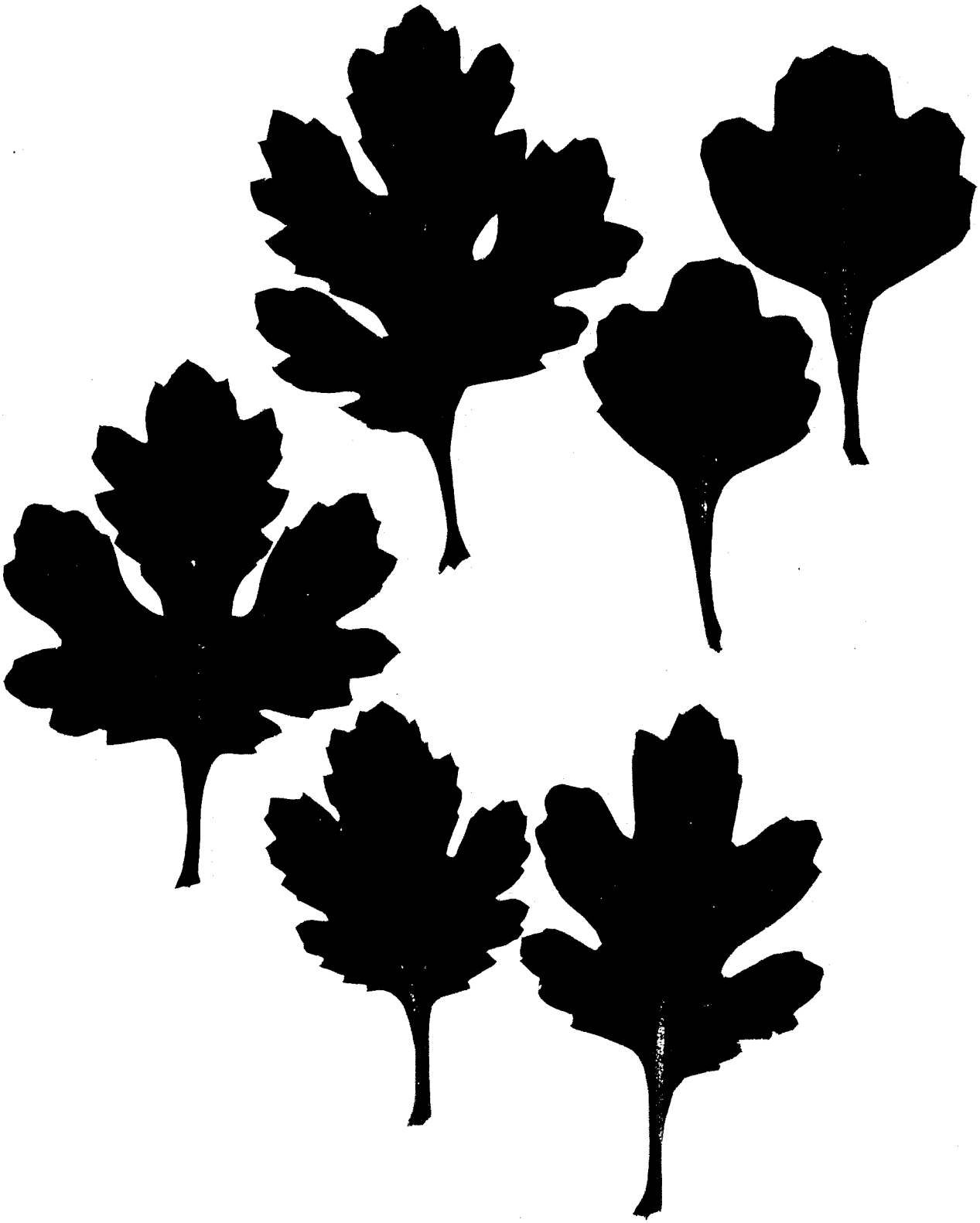

* * * * *